United States Patent
Pontiga et al.

(10) Patent No.: US 8,180,456 B2
(45) Date of Patent: May 15, 2012

(54) SYSTEMS AND METHODS TO CONFIGURE A MULTI-ELECTRODE LEAD

(75) Inventors: Christopher Pontiga, Sunnyvale, CA (US); Youngjian Wu, Sunnyvale, CA (US); Pajhand Iranitalab, San Ramon, CA (US); April Pixley, Los Altos, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 375 days.

(21) Appl. No.: 12/537,936

(22) Filed: Aug. 7, 2009

(65) Prior Publication Data

US 2010/0312298 A1  Dec. 9, 2010

Related U.S. Application Data

(60) Provisional application No. 61/185,519, filed on Jun. 9, 2009.

(51) Int. Cl.
*A61N 1/00* (2006.01)

(52) U.S. Cl. .................................................. 607/59

(58) Field of Classification Search ............... 607/9, 59, 607/27, 60
See application file for complete search history.

(56) References Cited

U.S. PATENT DOCUMENTS

| | | | |
|---|---|---|---|
| 4,922,607 A | 5/1990 | Doan | |
| 4,995,389 A | 2/1991 | Harris | |
| 5,246,014 A | 9/1993 | Williams | |
| 5,350,410 A | 9/1994 | Kleks | |
| 5,584,873 A | 12/1996 | Shoberg | |
| 5,814,089 A | 9/1998 | Stokes | |
| 5,948,014 A | 9/1999 | Valikai | |
| 6,141,588 A | 10/2000 | Cox | |
| 6,466,810 B1 | 10/2002 | Ward | |
| 6,546,288 B1 | 4/2003 | Levine | |
| 6,640,136 B1 | 10/2003 | Helland | |
| 6,882,887 B1 | 4/2005 | Shelchuk | |
| 6,978,178 B2 | 12/2005 | Sommer | |
| 7,027,852 B2 | 4/2006 | Helland | |
| 7,096,066 B1 | 8/2006 | Turcott | |
| 7,123,969 B1 | 10/2006 | Chitre | |
| 7,214,189 B2 | 5/2007 | Zdeblick | |
| 2006/0058588 A1 | 3/2006 | Zdeblick | |
| 2006/0085039 A1 | 4/2006 | Hastings | |
| 2006/0135999 A1 | 6/2006 | Bodner | |
| 2007/0150037 A1 | 6/2007 | Hastings | |
| 2007/0150038 A1 | 6/2007 | Hastings | |
| 2009/0062880 A1* | 3/2009 | Li et al. | 607/32 |
| 2011/0022113 A1* | 1/2011 | Zdeblick et al. | 607/30 |
| 2011/0034964 A1* | 2/2011 | Bi et al. | 607/5 |

FOREIGN PATENT DOCUMENTS

WO  WO 9826840  6/1998
WO  WO 2006065394  6/2006

* cited by examiner

*Primary Examiner* — Scott Getzow
(74) *Attorney, Agent, or Firm* — Steven M. Mitchell

(57) ABSTRACT

Methods and systems are provided for configuring a Multi-Electrode Lead (MEL) that includes N groups of electrodes, with each of the N groups of electrodes including at least M electrodes, where $N \geq 2$ and $M \geq 2$. Sent via the MEL is a first communication sequence of bits that includes N groups of bits, with each of the N groups of bits corresponding to a different one of the N groups of electrodes and specifying which electrode(s), if any, within the group of electrodes is to be configured as an anode. Also sent via the MEL is a second communication sequence of bits that includes N further groups of bits, with each of the N further groups of bits corresponding to a different one of the N groups of electrodes and specifying which electrode(s), if any, within the group of electrodes is to be configured as a cathode.

20 Claims, 7 Drawing Sheets

SYSTEMS AND METHODS TO CONFIGURE A MULTI-ELECTRODE LEAD

This application claims priority under 35 U.S.C. §119(e) to U.S. Provisional Patent Application No. 61/185,519, filed Jun. 9, 2009, which is incorporated herein by references.

FIELD OF THE INVENTION

Embodiments of the present invention relate to implantable cardiac systems and leads for use therewith. More specifically, embodiments of the present invention relate to systems and methods to configure a Multi-Electrode Lead (MEL).

BACKGROUND OF THE INVENTION

In the normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A-V) node and a ventricular conduction system causing a depolarization known as an R-wave and the resulting ventricular chamber contractions.

Disruption of this natural pacing and conduction system as a result of aging or disease can be successfully treated by artificial cardiac pacing using implantable cardiac stimulation devices, including pacemakers and implantable defibrillators, which deliver rhythmic electrical pulses or anti-arrhythmia therapies to the heart at a desired energy and rate. A cardiac stimulation device is electrically coupled to the heart by one or more leads possessing one or more electrodes in contact with the heart muscle tissue (myocardium). One or more heart chambers may be electrically stimulated depending on the location and severity of the conduction disorder.

A stimulation pulse delivered to the myocardium must be of sufficient energy to depolarize the tissue, thereby causing a contraction, a condition commonly known as "capture". In early pacemakers, a fixed, high-energy pacing pulse was delivered to ensure capture. While this approach is straight-forward, it quickly depletes battery energy and can result in patient discomfort due to extraneous extracardiac stimulation, e.g., of surrounding skeletal muscle tissue, the patient's phrenic nerve or the patient's diaphragm.

The "capture threshold" is defined as the lowest stimulation pulse energy at which capture occurs. By stimulating the heart chambers at or just above this threshold, comfortable and effective cardiac stimulation can be provided without unnecessary depletion of battery energy. The capture threshold, however, is extremely variable from patient-to-patient due to variations in electrode systems used, electrode positioning, physiological and anatomical variations of the heart itself, and so on. Furthermore, a capture threshold may vary over time within a patient as, for example, fibrotic encapsulation of an electrode can occur after implantation of the electrode.

Implantable lead(s), attached to an implantable cardiac device (ICD), such as a pacemaker, is/are used to deliver such stimulation pulses to the myocardium. Some such leads are Multi-Electrode Leads (MELs), meaning they include multiple electrodes for use in pacing and/or sensing. MELs allow for more flexibility in pacing and sensing, as compared to single electrode leads. Generally, the more electrodes on a lead, the more flexibility provided. However, a challenge when using leads with greater numbers of electrodes is increased complexity when setting up the electrode configuration. For example, one left-sided lead design includes four electrode arrays (also referred to as groups or bands) with four electrodes each, thus resulting in a single lead with sixteen electrodes. An example of an electrode that can include sixteen (and even more) electrodes is disclosed in U.S. Patent Publication No. 2006/0058588 (U.S. patent application Ser. No. 11/219,305), entitled "Methods and Apparatus for Tissue Activation and Monitoring" (Zdeblick), published Mar. 16, 2006 (filed Sep. 1, 2005), which is incorporated herein by reference. With such a complex MEL there can be hundreds and possibly thousands of different cathode-anode combinations (also referred to as cathode-anode electrode configurations).

Presuming it takes on the order of about 90 seconds to test each possible cathode-anode electrode configuration, it would take hours upon hours for a clinician to test all possible electrode configurations for MELs having numerous electrodes. This would be true even if the clinician used an auto set-up programmer, if the programmer were to try to test all possible combinations.

Another challenge when using leads with greater numbers of electrodes is the limitation to the number of groups of electrodes that can be programmed in a single pacing cycle. This limitation poses a drastic drawback on the system because fewer groups of electrodes can be programmed in a single pacing cycle and to program more groups of electrodes requires two or more pacing cycles. This poses a problem because it may leave the patient paced in an undesired configuration for a pacing cycle. This may cause phrenic stimulation, triggering the patient to hiccup every time (or at least some of the times) the lead is programmed. This can occur as little as every follow-up, or as much as once daily during a daily lead configuration check and/or reprogramming.

Accordingly, it would be beneficial if more efficient methods and systems were developed for assisting with the configuration of such MELs.

SUMMARY OF THE INVENTION

Embodiments of the present invention relate to methods and systems for expediting set-up of a Multi-Electrode Lead (MEL). In accordance with specific embodiments, such MEL includes N groups of electrodes, with each of the N groups including at least M electrodes, where N≧2 and M is ≧2.

Specific embodiments relate to methods that include sending, via the MEL, a first communication sequence of bits that includes N groups of bits, with each of the N groups of bits corresponding to a different one of the N groups of electrodes and specifying which electrode(s), if any, within the group of electrodes is to be configured as an anode. In an embodiment, a second communication sequence of bits that includes N further groups of bits can be sent via the MEL, with each of the N further groups of bits corresponding to a different one of the N groups of electrodes and specifying which electrode(s), if any, within the group of electrodes is to be configured as a cathode. In accordance with an embodiment, either the first or second communication sequence of bits can be sent before the other.

In accordance with specific embodiments, the first communication sequence includes, in addition to the N groups of bits, one or more bits that identify the first communication sequence as being used to configure electrodes as an anode. In an embodiment, the first communication sequence includes header bits that identify a start of the first communication sequence and trailer bits that identify an end of the first communication sequence. In accordance with an embodiment, within the first communication sequence, the one or more bits that identify the first communication sequence as being used to configure electrodes as an anode follow the header bits, the N groups of bits follow the one or more bits that identify the first communication sequence as being used to configure electrodes as an anode, and the trailer bits follow the N groups of bits.

In accordance with an embodiment, the second communication sequence includes, in addition to the N further groups of bits, one or more bits that identify the second communication sequence as being used to configure electrodes as a cathode. In accordance with an embodiment, the second communication sequence also includes header bits that identify the start of the second communication sequence and trailer bits that identify the end of the second communication sequence. In an embodiment, within the second communication sequence, the one or more bits that identify the second communication sequence as being used to configure electrodes as a cathode follow the header bits, the N further groups of bits follow the one or more bits that identify the second communication sequence as being used to configure electrodes as a cathode, and the trailer bits follow the N further groups of bits.

In accordance with an embodiment, each bit, within each group of bits of the first communication sequence that corresponds to one of the N groups of electrodes, has a bit-location that corresponds to one of the electrodes within the group of electrodes, and has a bit-type that specifies whether or not the electrode corresponding to the bit-location is to be configured as an anode. In accordance with an embodiment, for the bits within the N groups of bits of the first communication sequence there are two possible bit-types, one specifying that an electrode is to be configured as an anode, and another specifying that the electrode is not to be configured as an anode. In accordance with an embodiment, each bit, within each further group of bits of the second communication sequence that corresponds to one of the N groups of electrodes, has a bit-location that corresponds to one of the electrodes within the group of electrodes, and has a bit-type that specifies whether or not the electrode corresponding to the bit-location is to be configured as a cathode. In accordance with an embodiment, the two possible bit types in the first and second communication sequences include a 0 bit type and a 1 bit type.

This summary is not intended to be a complete description of, or limit the scope of, the invention. Alternative and additional features, aspects and objects of the invention can be obtained from a review of the specification, figures and the claims.

DETAILED DESCRIPTION OF THE INVENTION

Figure 1:
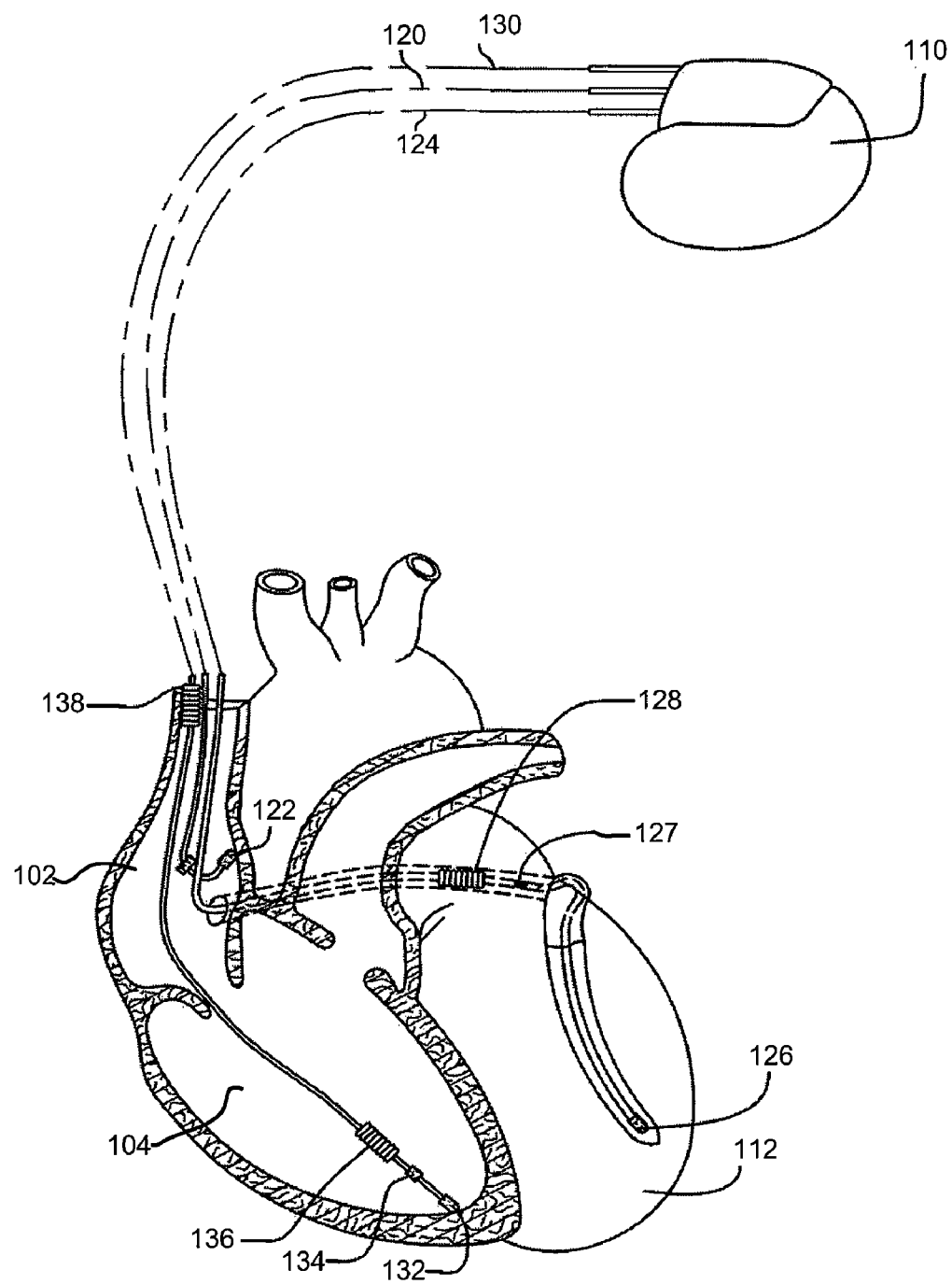
FIG. 1 is a simplified, partly cutaway view illustrating an exemplary implantable cardiac stimulation device in electrical communication with at least three leads implanted into a patient's heart for delivering multi-chamber stimulation and shock therapy.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

It would be apparent to one of skill in the art reading this description that the various embodiments of the present invention, as described below, may be implemented in many different embodiments of hardware, software, firmware, and/ or the entities illustrated in the figures. Any actual software, firmware and/or hardware described herein is not limiting of the present invention. Thus, the operation and behavior of the embodiments of the present invention will be described with the understanding that modifications and variations of the embodiments are possible, given the level of detail presented herein.

Exemplary Implantable Cardiac Stimulation Device

FIG. 1 illustrates an exemplary cardiac stimulation device 110 in electrical communication with a patient's heart 112 by way of three leads 120, 124 and 130 suitable for sensing cardiac electrogram signals and also delivering multi-chamber stimulation and shock therapy. To sense atrial cardiac signals and to provide right atrial chamber stimulation therapy, the cardiac stimulation device 110 is coupled to an implantable right atrial lead 120 having at least an atrial tip electrode 122, which typically is implanted in the patient's right atrial appendage. To sense left atrial and ventricular cardiac signals and to provide left-chamber pacing therapy, the cardiac stimulation device 110 is coupled to a "coronary sinus" lead 124 designed for placement in the "coronary sinus region" via the coronary sinus so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, the coronary sinus lead 124 is designed to receive atrial and ventricular cardiac signals and to deliver left ventricular pacing therapy using at least a left ventricular tip electrode 26, left atrial pacing therapy using at least a left atrial ring electrode 127, and shocking therapy using at least a left atrial coil electrode 128.

The cardiac stimulation device 110 is also shown in electrical communication with the patient's heart 112 by way of an implantable right ventricular lead 130 having, in this embodiment, a right ventricular tip electrode 132, a right ventricular ring electrode 134, a right ventricular (RV) coil electrode 136, and an SVC coil electrode 138. Typically, the right ventricular lead 130 is transvenously inserted into the heart 112 so as to place the right ventricular tip electrode 132 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals, and delivering stimulation in the form of pacing and shock therapy to the right ventricle. As will be appreciated from the discussion below, MELs, such as but not limited to the MELs discussed with reference to FIGS. 4A-4C, can be used in place of the more conventional leads 120, 124 and/or 130 shown in FIG. 1.

Figure 2:
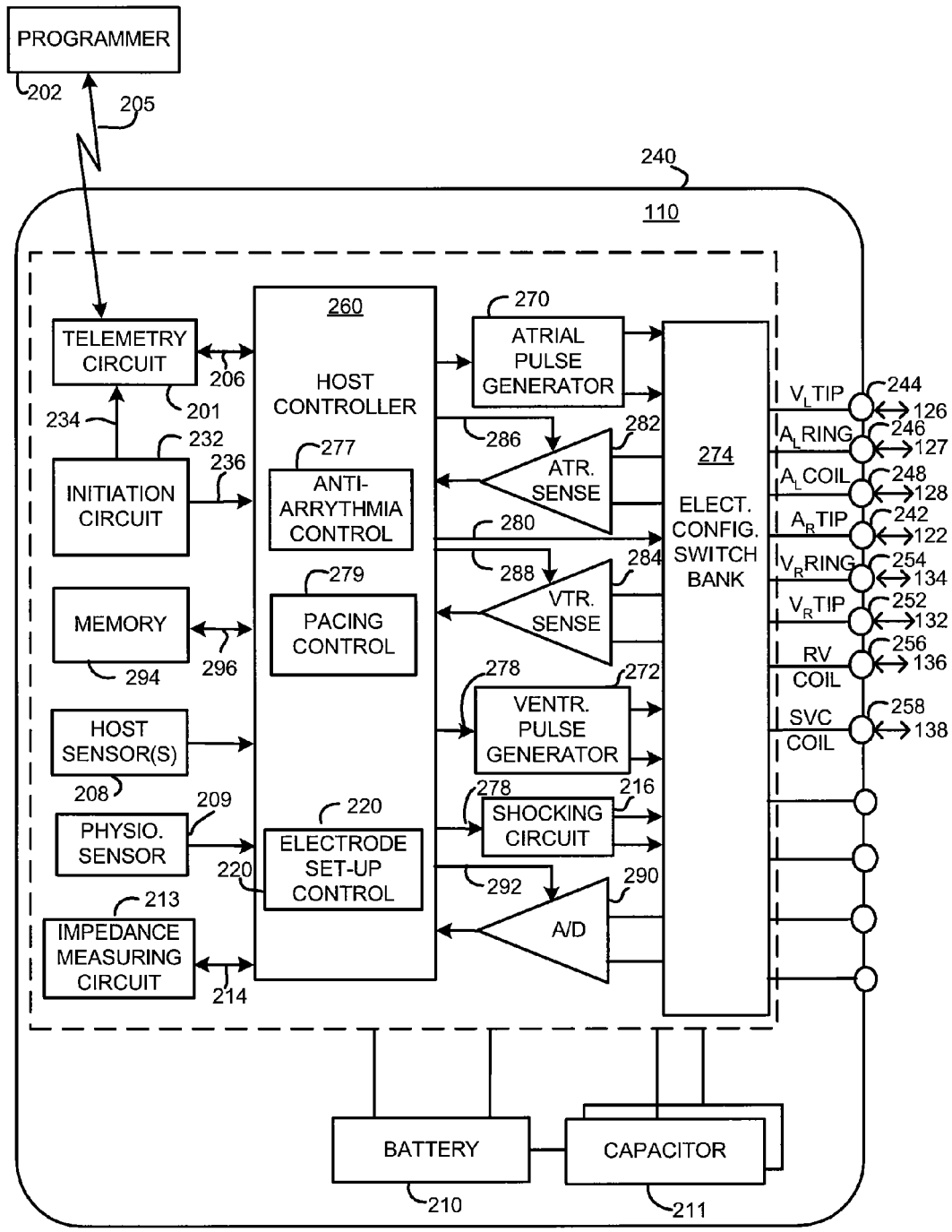
FIG. 2 is a functional block diagram of the exemplary multi-chamber implantable cardiac stimulation device of FIG. 1, illustrating the basic elements that provide cardioversion, defibrillation and/or pacing stimulation in four chambers of the heart.

FIG. 2 illustrates a simplified block diagram of the multi-chamber implantable cardiac stimulation device 110 which is capable of sensing cardiac electrogram signals, and also treating both fast and slow arrhythmias with stimulation therapy, including cardioversion, defibrillation, pacing stimulation. While a particular multi-chamber cardiac stimulation device is shown, this is for illustration purposes only and one of skill in the art could readily duplicate, eliminate or disable the appropriate circuitry in any desired combination to provide a device capable of sensing cardiac electrogram signals, treating the appropriate chamber(s) with cardioversion, defibrillation and/or pacing stimulation without departing from the scope of the invention.

Referring to FIG. 2, cardiac stimulation device 110 includes a housing 240 which is often referred to as a "can", "case" or "case electrode", and which may be programmably selected to act as the return electrode for all "unipolar" modes. Housing 240 may be used as a return electrode alone or in combination with one or more of the coil electrodes 128, 136, or 138, for shocking purposes. Housing 240 further includes a connector (not shown) having a plurality of terminals, 242, 244, 246, 248, 252, 254, 256, and 258 (shown schematically and, for convenience, the names of the exemplary electrodes to which they are connected are shown next to the terminals).

Figure 4A:
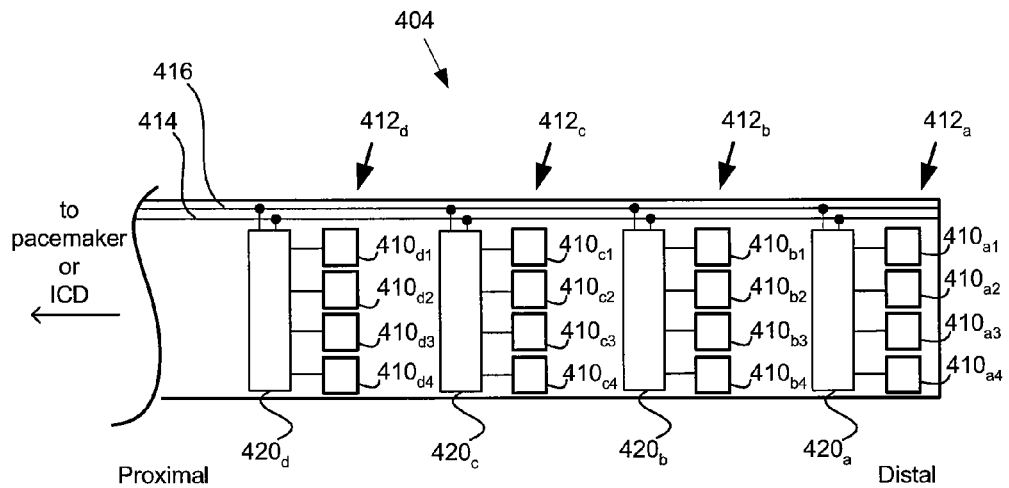
FIGS. 4A-4C schematically illustrate portions of exemplary Multi-Electrode Leads with which embodiments of the present invention can be useful.
Figure 4B:
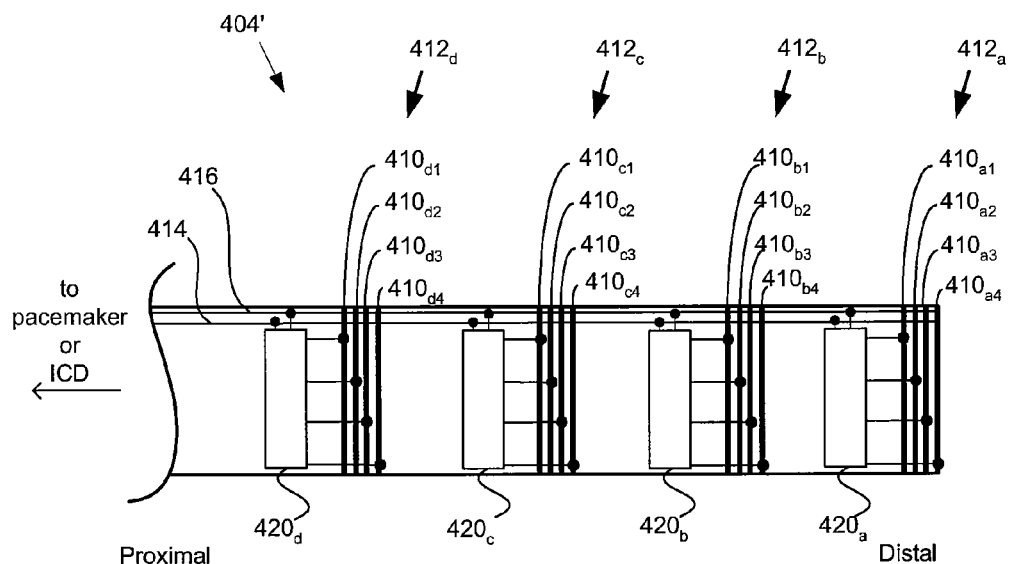
Figure 4C:
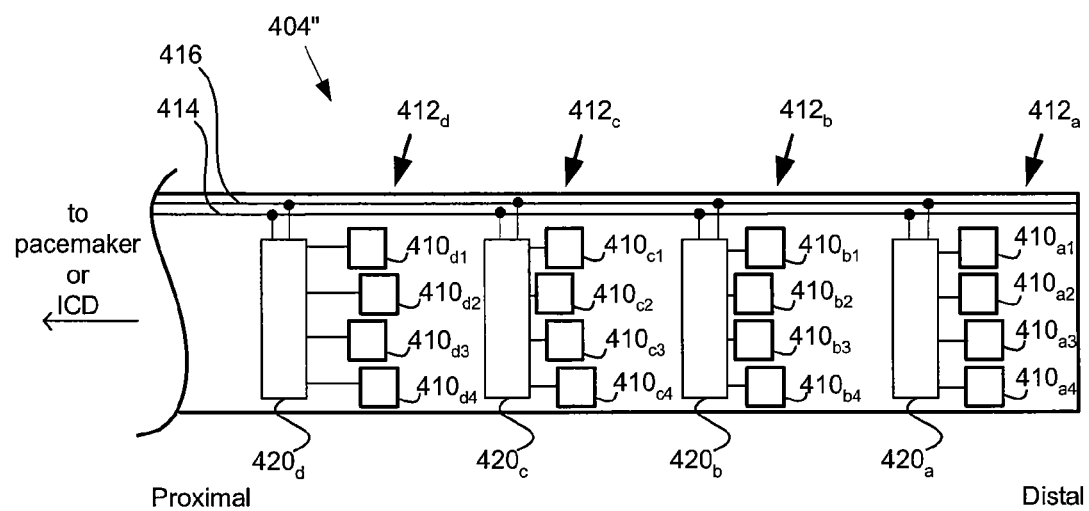

To achieve right atrial sensing and pacing, the connector includes at least a right atrial tip terminal 242 adapted for connection to the right atrial (AR) tip electrode 122. To achieve left chamber sensing, pacing and/or shocking, the connector includes at least a left ventricular (VL) tip terminal 244, a left atrial (AL) ring terminal 246, and a left atrial (AL) shocking terminal (coil) 248, which are adapted for connection to the left ventricular tip electrode 126, the left atrial ring electrode 127, and the left atrial coil electrode 128, respectively. To support right chamber sensing, pacing and/or shocking, the connector further includes a right ventricular (VR) tip terminal 252, a right ventricular (VR) ring terminal 254, a right ventricular (RV) shocking terminal (coil) 256, and an SVC shocking terminal (coil) 258, which are adapted for connection to the right ventricular tip electrode 132, right ventricular ring electrode 134, the RV coil electrode 136, and the SVC coil electrode 138, respectively. Where MELs, such as the ones described below with reference to FIGS. 4A-4C are being used, as few as two terminals can be used for each lead (i.e., one terminal for each conductor of a bus of the MEL).

At the core of cardiac stimulation device 110 is a programmable microcontroller, host controller 260, which controls the various modes of stimulation therapy. As is well known in the art, host controller 260 can include a microprocessor, or equivalent control and switching circuitry or processor, designed for controlling the delivery of stimulation therapy, and may further include RAM or ROM memory, logic and timing circuitry, state machine circuitry, and I/O circuitry. Typically, host controller 260 includes the ability to process or monitor input signals (data) as controlled by program code stored in a designated block of memory. The details of the design and operation of host controller 260 are not critical to the present invention. Rather, any suitable host controller 260 may be used that carries out the functions described herein. The use of microprocessor-based control circuits for performing timing and data analysis functions is well known in the art.

As shown in FIG. 2, an atrial pulse generator 270 and a ventricular pulse generator 272 generate pacing stimulation pulses for delivery by the right atrial lead 120, the right ventricular lead 130, and/or the coronary sinus lead 124 via a switch bank 274. It is understood that in order to provide stimulation therapy in each of the four chambers of the heart, the atrial pulse generator 270 and the ventricular pulse generator 272 may include dedicated, independent pulse generators, multiplexed pulse generators, or shared pulse generators. The atrial pulse generator 270 and the ventricular pulse generator 272 are controlled by host controller 260 via appropriate control signals 276 and 278, respectively, to trigger or inhibit the stimulation pulses. In an embodiment, the atrial pulse generator 270 and the ventricular pulse generator 272 are adapted to generate stimulation pulses that are delivered via the MEL, and configured in accordance with a first and second communication sequence, as described in more detail in FIGS. 5-6.

Host controller 260 further includes pacing control unit 279 which is used to control the timing of such stimulation pulses (e.g., pacing rate, atrio-ventricular (A-V) delay, atrial interconduction (A-A) delay, ventricular interconduction (V-V) delay, pacing mode, etc.), as well as to keep track of the timing of refractory periods, PVARP intervals, noise detection windows, evoked response windows, alert intervals, marker channel timing, etc.

The switch bank 274 includes a plurality of electrically configurable switches for connecting the desired electrodes to the appropriate I/O circuits, thereby providing complete electrode programmability. Accordingly, the switch bank 274, in response to a control signal 280 from host controller 260, determines the polarity of the stimulation pulses (e.g., unipolar, bipolar, combipolar, etc.) by selectively closing the appropriate combination of switches (not shown) as is known in the art. If multiple RV electrodes are employed to generate a single averaged ventricular signal, then switch bank 274 is configured to allow the paralleling (or averaging) of the multiple RV electrodes to simulate a large electrode for accurate sensing of the T-wave. Alternatively (or additionally) each group of electrodes of a MEL can include its own switching circuitry, as described in more detail below.

Atrial sensing circuits 282 and ventricular sensing circuits 284 may also be selectively coupled to the right atrial lead 120, coronary sinus lead 124, and the right ventricular lead 130, through the switch bank 274, for detecting the presence of cardiac activity in each of the four chambers of the heart. Accordingly, the atrial and ventricular sensing circuits 282 and 284 may include dedicated sense amplifiers, multiplexed amplifiers, or shared amplifiers. The switch bank 274 can determine the "sensing polarity" of the cardiac signal by selectively closing the appropriate switches. In this way, the clinician may program the sensing polarity independent of the stimulation polarity. Each of the sensing circuits, 282 and 284 preferably employ one or more low power, precision amplifiers with programmable gain and/or automatic gain control, bandpass filtering, and a threshold detection circuit, to selectively sense the cardiac signal of interest. The automatic gain control enables the cardiac stimulation device 110 to deal effectively with the difficult problem of sensing the low amplitude signal characteristics of atrial or ventricular fibrillation.

The outputs of the atrial and ventricular sensing circuits 282 and 284 are connected to host controller 260 for triggering or inhibiting the atrial and ventricular pulse generators 270 and 272, respectively, in a demand fashion, in response to the absence or presence of cardiac activity, respectively, in the appropriate chambers of the heart. The atrial and ventricular sensing circuits 282 and 284, in turn, receive control signals over signal lines 286 and 288 from host controller 260, for controlling the gain, threshold, polarization charge removal circuitry (not shown), and the timing of any blocking circuitry (not shown) coupled to the inputs of the atrial and ventricular sensing circuits 282 and 284.

Cardiac signals are also applied to the inputs of an analog-to-digital (A/D) data acquisition system 290. Data acquisition system 290 is configured to acquire intracardiac electrogram signals, convert the raw analog data into digital signals, and store the digital signals for later processing and/or telemetric transmission to an external device 202. Data acquisition system 290 is coupled to the right atrial lead 120, the coronary sinus lead 124, and the right ventricular lead 130 through switch bank 274 to sample cardiac signals across any pair of desired electrodes. Data acquired by data acquisition system 290 (and optionally stored) can be used for subsequent analysis to guide the programming of the device, appropriately adjust pacing interval parameters, select optimum pacing intervals, and/or select appropriate anti-arrhythmia therapy.

Advantageously, data acquisition system 290 may be coupled to host controller 260 or other detection circuitry, for detecting an evoked response from the heart 112 in response to an applied stimulus, thereby aiding in the detection of "capture". Capture occurs when an electrical stimulus applied to the heart is of sufficient energy to depolarize the cardiac tissue, thereby causing the heart muscle to contract. Host controller 260 detects a depolarization signal during a window following a stimulation pulse, the presence of which indicates that capture has occurred. Host controller 260 enables capture detection by triggering the ventricular pulse generator 272 to generate a stimulation pulse, starting a capture detection window using the timing circuitry within host controller 260, and enabling data acquisition system 290 via control signal 292 to sample the cardiac signal that falls in the capture detection window and, based on the amplitude of the sampled cardiac signal, determines if capture has occurred.

One function of the cardiac stimulation device 110 can be to operate as an implantable cardioverter/defibrillator ("ICD") device. That is, cardiac stimulation device 110 detects the occurrence of an arrhythmia, and automatically applies an appropriate electrical shock therapy to the heart aimed at terminating the detected arrhythmia. To this end, anti-arrhythmia control unit 277 of control host controller 260 further controls a shocking circuit 216 by way of a control signal 218. The shocking circuit 216 generates shocking pulses of low (up to 0.5 joules), moderate (0.5-10 joules), or high (11-40 joules) energy, as controlled by host controller 260. Such shocking pulses are applied to the patient's heart through at least two shocking electrodes, as shown in this embodiment, selected from the left atrial coil electrode 128, the RV coil electrode 136, and/or the SVC coil electrode 138 (FIG. 1). As noted above, the housing 140 may act as an active electrode in combination with the RV electrode 136, or as part of a split electrical vector using the SVC coil electrode 138 or the left atrial coil electrode 128 (e.g., using the RV electrode as a common electrode). The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

For arrhythmia detection, the anti-arrhythmia control unit 277 of host controller 260 utilizes the atrial and ventricular sensing circuits 282 and 284 to sense cardiac signals, for determining whether a rhythm is physiologic or pathologic. The timing intervals between sensed events (e.g., P-waves, R-waves, and depolarization signals associated with fibrillation which are sometimes referred to as "F-waves" or "Fib-waves") are then classified by anti-arrhythmia control unit 277 of host controller 260 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Host controller 260 is further coupled to a memory 294 by a suitable data/address bus 296, where the programmable operating parameters used by host controller 260 are stored and modified, as required, in order to customize the operation of the cardiac stimulation device 110 to suit the needs of a particular patient. Such operating parameters define, for example, pacing pulse amplitude, pulse duration, electrode polarity, rate, sensitivity, automatic features, arrhythmia detection criteria, pacing mode, and the amplitude, waveshape and vector of each shocking pulse to be delivered to the patient's heart 112 within each respective tier of therapy. A feature of the cardiac stimulation device 110 is the ability to sense and store a relatively large amount of data (e.g., from data acquisition system 290), which data may then be used for subsequent analysis and also guiding the programming of the cardiac stimulation device 110. The host controller 260 can also be connected to host sensor(s) 208, a physiologic sensor 209, and an impedance measuring circuit 213, as shown.

Advantageously, the operating parameters of the cardiac stimulation device 110 may be non-invasively programmed into the memory 294 through a telemetry circuit 201 in telemetric communication with an external programmer 202, such as a transtelephonic transceiver, or a diagnostic system analyzer. Additionally, telemetry circuit 201 may be used to guide the device 110 through electrode set-up algorithms of the present invention, which are discussed in more detail below.

A handshake signal can be sent from the programmer 202 (or other external device) to the telemetry circuit 201 so that the external device can be identified to the telemetry circuit 201 thereby defining what operations may be performed by the device. The programmer 202 can program the cardiac stimulation device 110 under the control of a physician as described in more detail with respect to FIG. 3. For examples of such programmers, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (this relates to transfer of EGM data) (McClure et al.), which patents are hereby incorporated herein by reference.

Cardiac stimulation device 110 further includes initiation circuit 232. Initiation circuit 232 may comprise magnet detection circuitry. Initiation circuit 232 is coupled to host controller 260 by connection 236 and/or to telemetry circuit 201 by connection 234. The purpose of the initiation circuit is to detect an initiation signal from outside the patient. For example, a magnet placed over the cardiac stimulation device 110 may be used as the initiation signal, which signal may be used by a clinician to initiate various test functions of the cardiac stimulation device 110 and/or to signal host controller 260 that an external programmer 202 is in place to receive or transmit data to host controller 260 through the telemetry circuit 201. Initiation circuit 232 may also be used to activate electrode set-up algorithms of the present invention.

An electrode set-up control 220 of host controller 260 can process EGM signals to monitor for capture during pacing and to measure R-waves during sensing. The electrode set-up control 220 can cause the performance of the steps 502 and 504 illustrated in FIG. 5, possibly under the control of an external device (e.g., an external programmer 202). Additionally, the electrode set-up control 220 can also configure electrodes in specific configurations, as instructed by an external device, such as the external programmer 202. This can be accomplished, e.g., by sending signals to the switch bank 274, and/or to switching circuitry of MELs where appropriate. The electrode set-up control 220, and/or a separate component, can also be used to detect capture thresholds. While shown as being part of the host controller 220, portions of the entire electrode set-up control 220 can be external to the controller 260, and can include software, firmware, hardware or combinations thereof.

Cardiac stimulation device 110 additionally includes a power source such as a battery 210 that provides operating power to all the circuits shown in FIG. 2. For a cardiac stimulation device 110, which employs shocking therapy, the battery 210 should be capable of operating at low current drains for long periods of time and also be capable of providing high-current pulses (for charging capacitor 211) when the patient requires a shock pulse. Battery 210 must preferably have a predictable discharge characteristic so that elective replacement time can be detected. Accordingly, cardiac stimulation device 110 can employ lithium/silver vanadium oxide batteries.

Exemplary Programmer

Figure 3:
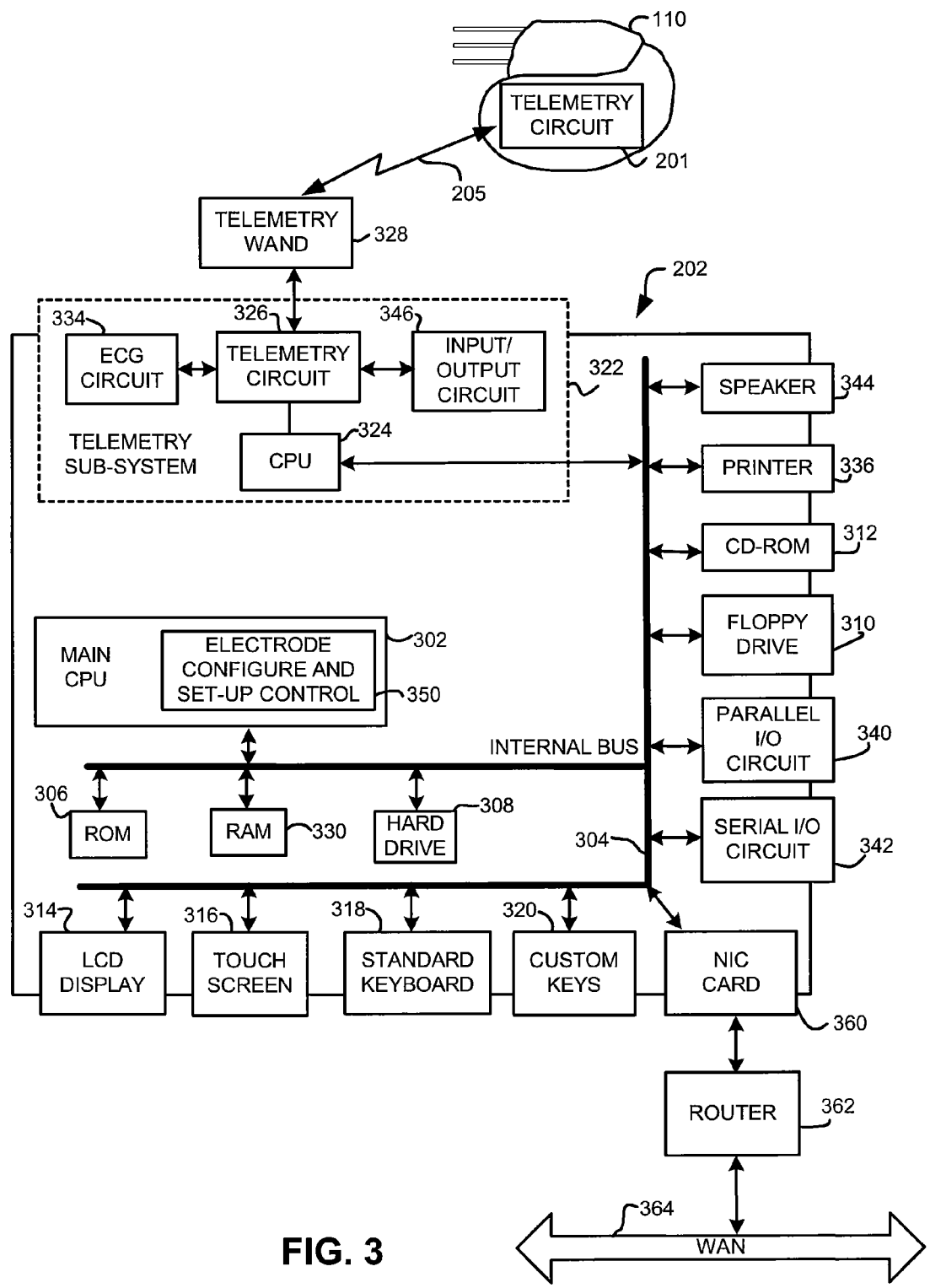
FIG. 3 is a functional block diagram illustrating components of an exemplary programmer for use in programming the implantable cardiac stimulation device of FIGS. 1 and 2.

FIG. 3 illustrates components of an exemplary programmer 202 for use in programming an implantable cardiac stimulation device, including setting up electrode configurations of an implantable cardiac stimulation device. The programmer 202 permits a physician or other authorized user to program the operation of the implantable cardiac stimulation device 110 and to retrieve and display information received from the implantable cardiac stimulation device 110 such as EGM data and device diagnostic data. Additionally, the programmer 202 may receive and display ECG data from separate external ECG leads that may be attached to the patient. Further, the programmer 220 is capable of causing the implantable cardiac stimulation device to perform functions necessary to complete certain electrode set-up algorithms of the present invention. Depending upon the specific programming of the programmer, programmer 202 may also be capable of processing and analyzing data received from the implantable cardiac stimulation device 110 and from ECG leads 332 to, for example, render preliminary diagnosis as to medical conditions of the patient or to the operations of the implantable cardiac stimulation device 110.

Now, considering the components of the programmer 202 by reference to FIG. 3, operations of the programmer 202 can be controlled by a CPU 302, which may be a generally programmable microprocessor or microcontroller or may be a dedicated processing device such as an Application Specific Integrated Circuit (ASIC) or the like. Software instructions to be performed by the CPU can be accessed via an internal bus 304 from a Read Only Memory (ROM) 306 and Random Access Memory (RAM) 330. Additional software may be accessed from a hard drive 308, floppy drive 310, and CD ROM drive 312, or other suitable permanent mass storage device. Depending upon the specific implementation, a Basic Input Output System (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 314 or other suitable computer display device. To this end, the CPU may, for example, display a menu of specific programming parameters of the implantable cardiac stimulation device 110 to be programmed or may display a menu of types of diagnostic data to be retrieved and displayed. In response thereto, the physician enters various commands via either a touch screen 316 overlaid on LCD display 314 or through a standard keyboard 318 supplemented by additional custom keys 320, such as an emergency VVI (EVVI) key. The EVVI key sets the implantable cardiac stimulation device 110 to a safe VVI mode with high pacing outputs. This ensures life-sustaining pacing operation in nearly all situations but by no means is it desirable to leave cardiac stimulation device 110 in the EVVI mode at all times.

Typically, the physician initially controls the programmer 202 to retrieve data stored within the implanted medical device and to also retrieve ECG data from ECG leads (examples discussed above with reference to FIGS. 1 and 2) coupled to the patient's myocardium. To this end, CPU 302 transmits appropriate signals to a telemetry circuit 322, which provides components for directly interfacing with implantable cardiac stimulation device 110. The telemetry subsystem 322 can include its own separate CPU 324 for coordinating the operations of the telemetry subsystem 322. The main CPU 302 of the programmer 202 communicates with telemetry subsystem CPU 324 via internal bus 304. The telemetry subsystem 322 additionally includes a telemetry circuit 326 connected to a telemetry wand 328, which cooperate to receive and transmit signals electromagnetically from telemetry circuit 201 of the implantable cardiac stimulation device 110. The telemetry wand 328 is placed over the chest of the patient near the implanted cardiac stimulation device 110 to permit reliable transmission of data, over telemetric link 205, between the telemetry wand and the implantable cardiac stimulation device 110. Typically, at the beginning of the programming session, the external programming device controls the implantable cardiac stimulation device 110 via appropriate signals generated by telemetry wand 328 to output all previously recorded patient and device diagnostic information. Patient diagnostic information includes, for example, measured physiological variables data, recorded EGM data and statistical patient data such as the percentage of paced versus sensed heartbeats. Device diagnostic data includes, for example, information representative of the operation of the implantable cardiac stimulation device 110 such as lead impedances, battery voltages, battery Recommended Replacement Time (RRT) information and the like. Data retrieved from the implantable cardiac stimulation device 110 is stored by the external programmer 202 either within a Random Access Memory (RAM) 330, a hard drive 308, within a floppy diskette placed within a floppy drive 310, etc. Additionally, or in the alternative, data may be permanently or semi-permanently stored within a Compact Disk (CD) or other digital media disk, if the overall system is configured with a drive for recording data onto digital media disks, such as a Write Once Read Many (WORM) drive.

Patient and device diagnostic data stored within the implantable cardiac stimulation device 110 can be transferred to the programmer 202. Further, the implantable cardiac stimulation device 110 can be instructed to perform an electrode set-up algorithm of the present invention, details of which are provided below.

The programmer 202 can also include a Network Interface Card ("NIC") 360 to permit transmission of data to and from other computer systems via a router 362 and Wide Area Network ("WAN") 364. Alternatively, the programmer 202 might include a modem for communication via the Public Switched Telephone Network (PSTN). Depending upon the implementation, the modem may be connected directly to internal bus 304 and may be connected to the internal bus via either a parallel port 340 or a serial port 342. Data transmitted from other computer systems may include, for example, data regarding medication prescribed, administered or sold to the patient.

The CPU 302 can include an electrode set-up control 350 that can control the performance of the steps 502 and 504 described below with reference to FIG. 5, and/or instruct the implantable stimulation device 110 to perform such steps. The electrode set-up control 350 of CPU 302 can operate in concert with the electrode set-up control 220 of device 110, or independent thereof. The programmer 202 receives data from the implantable cardiac stimulation device 110, including parameters representative of the current programming state of the implantable cardiac stimulation device 110. Under the control of the physician, programmer 202 displays the current programming parameters and permits the physician to reprogram the parameters. To this end, the physician enters appropriate commands via any of the aforementioned input devices and, under control of the CPU 302, the programming commands are converted to specific programming parameters for transmission to the implantable cardiac stimulation device 110 via the telemetry wand 328 to thereby reprogram the implantable cardiac stimulation device 110. Prior to reprogramming specific parameters, the physician may control the external programmer to display any or all of the data retrieved from the implantable cardiac stimulation device 110, including displays of ECGs, displays of electrodes that are candidates as cathodes and/or anodes, and statistical patient information. Any or all of the information displayed by programmer 202 may also be printed using a printer 336.

A speaker 344 is included for providing audible tones to the user, such as a warning beep in the event improper input is provided by the physician. Telemetry subsystem 322 may additionally include an input/output circuit 346 which can control the transmission of analog output signals, such as ECG signals output to an ECG machine or chart recorder. Other peripheral devices may be connected to the external programmer 202 via parallel port 340 or a serial port 342 as well. Although one of each is shown, a plurality of Input Output (IO) ports might be provided.

With the programmer 202 configured as shown, a physician or other authorized user can retrieve, process and display a wide range of information received from the implantable cardiac stimulation device 110 and reprogram the implantable cardiac stimulation device 110, including configurations of leads, if needed. The descriptions provided herein with respect to FIG. 3 are intended merely to provide an overview of the operation of the exemplary programmer 202 and are not intended to describe in detail every feature of the hardware and software of the device and are not intended to provide an exhaustive list of the functions performed by the device.

Exemplary Multi-Electrode Leads

FIG. 4A illustrates a portion of an exemplary MEL 404, which can be used with specific embodiments of the present invention. While not specifically shown in FIG. 4A, the lead 404 can be connected to the implantable cardiac stimulation device 110, e.g., in place of any of leads 120, 124 and/or 130. For the purpose of the following description, the lead 404 will be described as having a 4×4 matrix of electrodes, because the lead includes four arrays (also referred to as groups) of electrodes, each of which includes four electrodes 410. Each electrode 410 is electrically isolated from the other electrodes 410, but is capable of being electrically connected to other electrodes. Thus, exemplary lead 404 includes sixteen electrically isolated electrodes 410.

In accordance with an embodiment, electrodes within the same group share at least some common control and switching circuitry. Further, in accordance with an embodiment, electrodes within a same group are within 5 mm of one another, while electrodes within different groups are at least 10 mm from one another.

As shown in FIG. 4A, a first group of electrodes $412_a$, which is most distal from the implantable cardiac stimulation device 110, includes electrodes $410_{a1}$, $410_{a2}$, $410_{a3}$ and $410_{a4}$. A second group of electrodes $412_b$, which is more proximal to the implantable cardiac stimulation device 110, includes electrodes $410_{b1}$, $410_{b2}$, $410_{b3}$ and $410_{b4}$. Also shown are a third group of electrodes $412_c$ and a fourth group of electrodes $412_d$, including electrodes $410_{c1}$-$410_{c4}$ and $410_{d1}$-$410_{d4}$, respectively. The groups of electrodes are shown schematically, and are not drawn to scale. For example, it may be that each electrode 410, of a group of electrodes 412, actually occupies slightly less than 90 degrees of a ring around a lead. Alternatively, electrodes 412 of a group 410 can be a very closely spaced ring electrodes, e.g., as shown in FIG. 4B. FIG. 4C shows yet another example of groups 412 of electrodes 410. Other groups of electrodes are also possible, as one of ordinary skill in the art would appreciate from this description.

Each MEL (e.g., 404) is also shown as including conductors 414 and 416, which can collectively be referred to as a communication bus. It is also possible that such a bus can include more than two conductors.

Also, as shown in FIG. 4A, the first group of electrodes $412_a$ is connected to control and switching circuitry $420_a$. The second group of electrodes $412_b$ is connected to control and switching circuitry $420_b$. Also shown are a third group of electrodes $412_c$ and a fourth group of electrodes $412_d$, which are connected to control circuitries $412_c$ and $412_d$, respectively.

The control and switching circuitry 420 enables multiple electrodes to be selectively connected to the conductors 414 and 416. Signals can be sent via the conductors 414 and 416 from the implantable cardiac stimulation device 110 to the control and switching circuitry $420_a$-$420_d$, and to control which electrode(s) in groups $412_a$-$412_d$ are to be connected to the conductors 414 and 416. The same conductors 414 and 416 (or alternate conductors) can be used to deliver stimulation pulses to the various electrodes for pacing and/or shocking a patient's heart.

In accordance with an embodiment, the control and switching circuitry 420 associated with each group of electrodes can include, e.g., a shift register for shifting in bits of the communications sequences and/or a latch for latching bits of the communications sequences. Additionally, the control and switching circuitry 420 associated with each group of electrodes can include logic circuitry (e.g., a state machine, but not limited thereto) that can count wait states, identify which bits are intended for use by the group of electrodes and/or can identify the operation designated by an op-code (e.g., can identify whether an anode configuration or a cathode configuration is to be configured). The control and switching circuitry 420 associated with each group of electrodes can also include, or have associated with it, a charge pump for generating a voltage sufficient to power the control and switching circuitry 420 based on signals received via the conductors 414 and 416 (or alternate conductors) from the implantable cardiac stimulation device 110. The control and switching circuitry 420 can also include switches (e.g., transistor switches) that are controlled to configure specific electrodes of a group of electrodes, as an anode, a cathode, or as neither an anode or cathode.

Another example of a MEL is disclosed, for example, in U.S. Patent Publication No. 2006/0058588 (U.S. patent application Ser. No. 11/219,305), entitled "Methods and Apparatus for Tissue Activation and Monitoring" (Zdeblick), published Mar. 16, 2006 (filed Sep. 1, 2005), which is incorporated herein by reference above (referred to hereafter as "the '588 publication"). MELs of the '588 patent publication include what are referred to as "satellites", where each satellite essentially includes a group of electrodes with control and switching circuitry that enables any electrode of a group to be connected to one of two conductors. Stated another way, each group of electrodes can be said to include control and switching circuitry. Such control and switching circuitry is controlled by a controller associated with a cardiac stimulation device (e.g., pacemaker and/or ICD), to which the lead is attached. Digital signals can be sent via the two conductors from the controller to the control and switching circuitry, to thereby control which electrode(s) is/are to be connected to which of the two conductors. Additionally, analog signals can be sent via the two conductors between the pacemaker and electrodes for delivering pacing pulses and sensing. The '588 patent publication discloses that one such lead can include, e.g., eight satellites, with each satellite comprising four electrodes, which would result in a lead having thirty-two electrodes. The electrodes of the leads 404, 404' and 404" of FIGS. 4A-4C can be configured and controlled in a similar manner as those disclosed in the '588 patent publication.

FIGS. 4A-4C discussed above illustrate exemplary leads 404, 404' and 404" that each have four groups of electrodes, with each group of electrodes comprising four electrodes, resulting in each lead having a total of sixteen electrodes. Such leads can be used to implement embodiments of the present invention. When using a lead such as those in FIGS. 4A-4C, the cathode can be one or more electrode in a group, and the anode can be one or more electrode of that same group (which may, or may not be electrically connected with one or more electrode of another group). However, embodiments of the present invention are not limited to use with MELs that are similar to those described with reference to FIGS. 4A-4C. Rather, certain embodiments of the present invention can be used with any lead that includes multiple groups of electrodes, including those disclosed in the '588 patent publication.

These are just a few examples of MELs with which embodiments of the present invention can be used. However, embodiments of the present invention, unless stated otherwise, are not limited to use with the exemplary leads described herein.

Set-Up Algorithms

Figure 5:
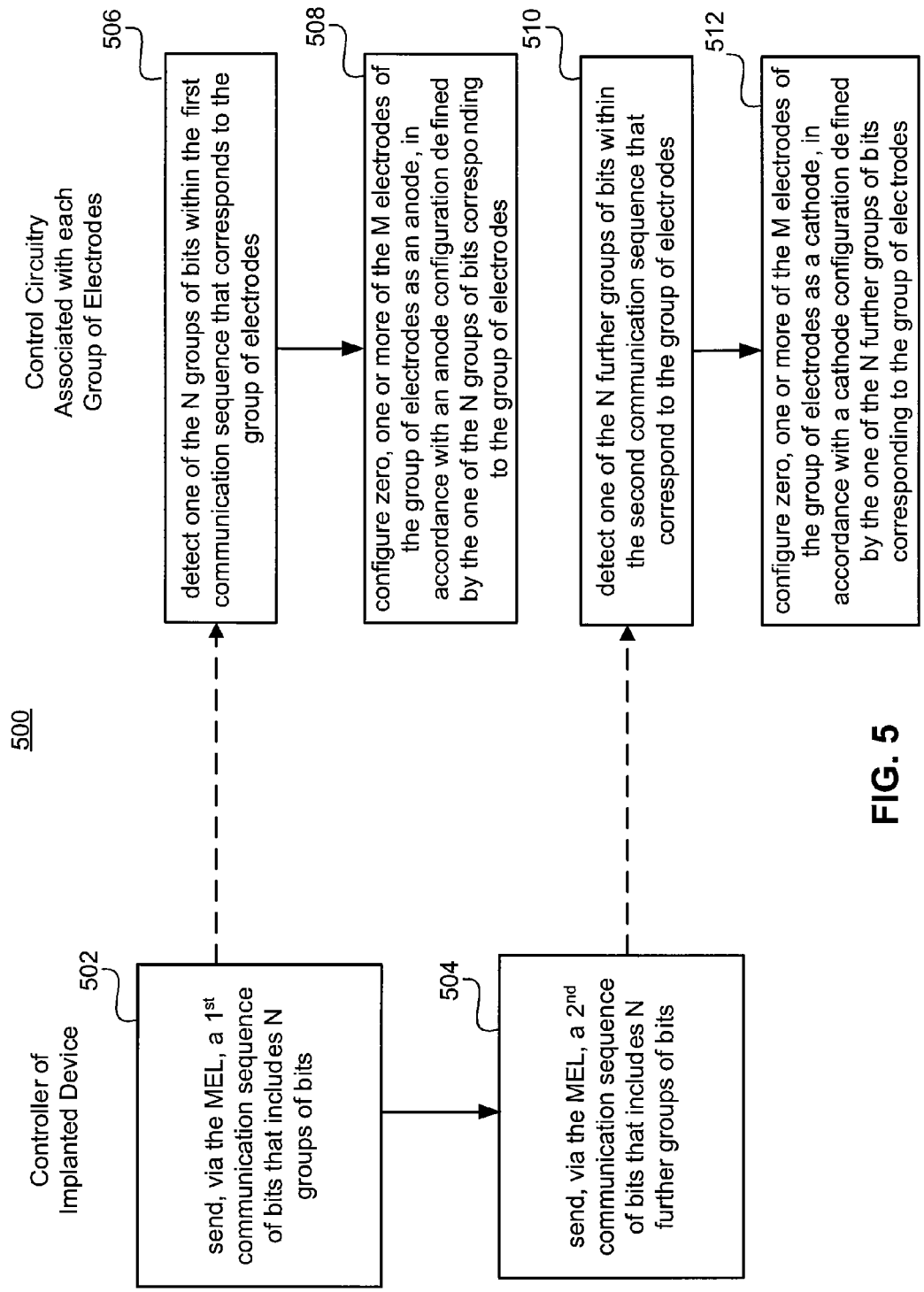
FIG. 5 is a high-level flow diagram that is used to explain the interaction between the controller of the implanted device and the control and switching circuitry associated with each group of electrodes.

Certain embodiments of the present invention shall now be summarized with reference to the high level flow diagram of FIG. 5. More specifically, embodiments of the present invention described with reference to FIG. 5 can be used to identify in an efficient manner cathode-anode electrode configurations that can be used to illustrate techniques for configuring a MEL (e.g., 404). Where embodiments of the present invention are summarized with reference to the high level flow diagrams, various algorithmic steps are summarized in individual 'blocks'. Such blocks describe specific actions or decisions that are made or carried out as the algorithm proceeds. Where a microcontroller (or equivalent) is employed, the flow diagrams presented herein provides the basis for a 'control program' that may be used by such a microcontroller (or equivalent) to effectuate the desired control of the implantable system. Those skilled in the art may readily write such a control program based on the flow diagram and other description presented herein. Embodiments of the present invention are not limited to the exact order and/or boundaries of the steps shown in the flow diagrams. In fact, many of the steps can be performed in a different order than shown, and many steps can be combined, or separated into multiple steps. All such variations are encompassed by the present invention. The only time order is important is where a step acts on the result of a previous step.

Such embodiments are for use with an implantable system that includes an implantable cardiac stimulation device (e.g., 110) to which is attached at least one MEL (e.g., 404) that includes N groups of electrodes, with each of the N groups including at least M electrodes, where $N \geq 2$ and M is $\geq 2$. Examples of such MELs were described above in the discussion of FIGS. 4A-4C and the discussion of the '588 publication. However, embodiments of the present invention are not limited to use with those exemplary leads. Further, it is noted that an MEL can be configured as an unipolar lead, with one or more electrodes of the MEL configured as the cathode, and the pacemaker and/or ICD housing (also known as "the can") configured as the anode. In such a case, zero electrodes of the MEL could be configured as the anode. Alternatively, one or more electrodes of the MEL can be configured as the anode, and the pacemaker and/or ICD housing can be configured as the cathode, in which case zero electrodes of the MEL could be configured as the cathode. Thus, regardless of how many electrodes the MEL has, it is possible that as few as one electrode can be configured as the cathode (or the anode), and zero electrodes of the MEL can be configured as the anode (or the cathode).

FIG. 5 is a high level flow diagram that is used to explain the interaction between the controller (e.g., 260 in FIG. 2) of the implanted device and the control and switching circuitry 420 associated with each group of electrodes. At the controller side of the implanted device, at step 502, sent via the MEL (e.g., 404) is a first communication sequence of bits, including N groups of bits, with each of the N groups of bits corresponding to a different one of the N groups of electrodes and specifying which electrode(s), if any, within the group of electrodes is to be configured as an anode.

At step 506, the control and switching circuitry 420 associated with each of the groups of electrodes detects a different one of the N groups of bits within the first communication sequence that corresponds to the group of electrodes. At step 508, the control and switching circuitry 420 associated with each of the groups of electrodes configures as an anode, zero, one or more of the M electrodes of the group of electrodes, in accordance with an anode configuration defined by the one of the N groups of bits corresponding to the group of electrodes.

It is possible that electrodes of different groups of electrodes are configured as an anode at the same time, which can be used to provide a "distributed" anode configuration. Benefits of using what is referred to as a "distributed" anode configuration, where one electrode of the anode is within the same group as the cathode electrode(s), but another electrode of the anode is in a different group than the cathode electrode(s), are discussed in commonly invented and commonly assigned U.S. patent application Ser. No. 11/688,941, entitled "Distributed Anode Cardiac Pacing and Sensing", filed Mar. 21, 2007 (Shelchuk) (Attorney Docket No. A07P3009), which is incorporated herein by reference. Embodiments of the present invention contemplate the use of a distributed anode. It is also possible that electrodes of different groups of electrodes are configured as a cathode at the same time.

At the controller side of the implanted device, at step 504, sent via the MEL (e.g., 404) is a second communication sequence of bits, including N further groups of bits, with each of the N further groups of bits corresponding to a different one of the N groups of electrodes and specifying which electrode(s), if any, within the group of electrodes is to be configured as a cathode. At step 510, the control and switching circuitry 420 associated with each of the groups of electrodes detects a different one of the N further groups of bits within the second communication sequence that corresponds to the group of electrodes. At step 512, the control and switching circuitry 420 associated with each of the groups of electrodes configures as a cathode, zero, one or more of the M electrodes of the group of electrodes, in accordance with a cathode configuration defined by the one of the N further groups of bits corresponding to the group of electrodes.

For a group of M electrodes (e.g., M=4), all of the M electrodes can be configured as an anode, none of the M electrodes can be configured as an anode, or a number between 0 and M of the electrodes can be configured as an anode. Similarly, for a group of M electrodes, all of the M electrodes can be configured as a cathode, none of the M electrodes can be configured as a cathode, or a number between 0 and M of the electrodes can be configured as a cathode. However, the same electrode can not be configured as both a cathode and anode at the same time, but may be at different times.

In an embodiment of the present invention, steps 502 and 504 can be performed in a different order than shown. For example, step 504 can be performed before step 502 such that the control and switching circuitry 420 configures as a cathode, zero, one or more of the M electrodes of the group of electrodes before configuring zero, one or more of the M electrodes of the group of electrodes as an anode. In an embodiment, steps 502 and 504 can be preformed consecutively, such that the first bit of the second communication sequence immediately follows (i.e., the sending of the first and second communication sequences are performed without any time delay therebetween) the last bit of the first communication sequence. In an embodiment, there can be some amount of time between the sending of the first communication sequence and the sending of the second communication sequence (e.g., the time between the sending of the first and second communication sequences can be 1 or more beats of the heart, but is not limited thereto). It is also possible that other communications sequences than those described above can be sent between the sending of the first and second communication sequences described above.

In accordance with an embodiment of the invention, in a communication sequence, the first of the N groups of bits sent can be used to configure the group of electrodes most proximal the implantable cardiac stimulation device (e.g., 110), and the last of the N groups of bits sent can be used to configure the group of electrodes most distal the implantable cardiac stimulation device. The configuring of the electrodes most proximal and most distal to the implantable cardiac stimulation device can be reversed, such that the first of the N groups of bits sent can be used to configure the group of electrodes most distal the implantable cardiac stimulation device, and the last of the N groups of bits sent can be used to configure the group of electrodes most proximal the implantable stimulation device.

Figure 6A:
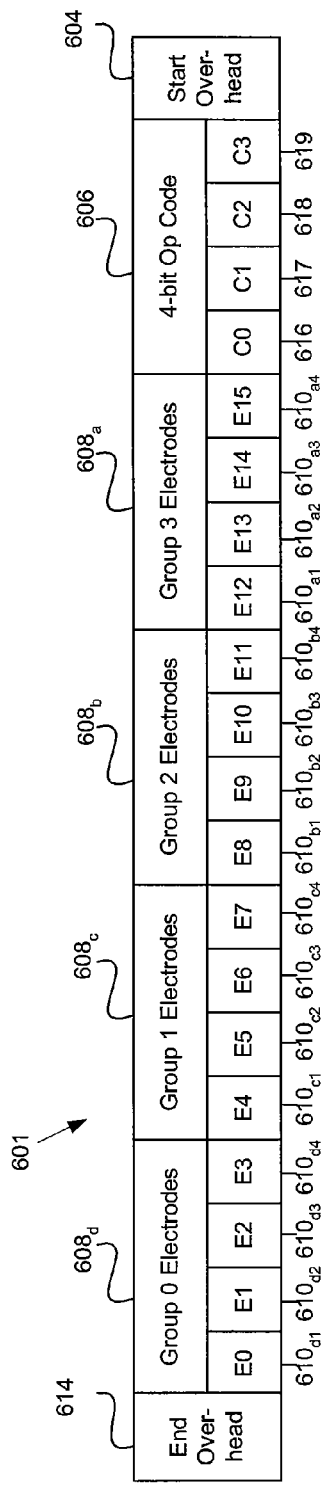
FIGS. 6A-6B schematically illustrate an embodiment of the first and second communication sequences.

FIG. 6A schematically illustrates a first communication sequence of bits 601 that can be sent at step 502. The first communication sequence of bits 601 comprises a start overhead 604 that identifies a start of the first communication sequence of bits 601 and an end overhead 614 that identifies an end of the first communication sequence of bits 601.

Following the start overhead 604 is a 4-bit op code 606 that includes bit positions 616-619. The 4-bit op code can instruct the control and switching circuitry 420 to perform one of a plurality of commands. For example, the MEL being configured using the communication sequence of bits 601 can include the 4-bit op code 606 that instructs the control and switching circuitry 420 that the communication sequence of bits 601 is being used to configure zero, one or more electrodes of a group of electrodes as an anode. The op code 606 can alternatively include more or less than 4-bits.

A first group of bits $608_a$ includes bit positions $610_{a1}$-$610_{a4}$. A second group of bits $608_b$ includes bit positions $610_{b1}$-$610_{b4}$. Also shown are a third group of bits $608_c$ and a fourth group of bits $608_d$, including bit positions $610_{c1}$-$610_{c4}$ and $610_{d1}$-$610_{d4}$, respectively. Each bit, within each group of bits $608_a$-$608_d$ of the first communication sequence of bits 601 that corresponds to one of the N groups of electrodes, has a bit-location that corresponds to one of the electrodes within the group of electrodes, and has a bit-type that specifies whether or not the electrode corresponding to the bit-location is to be configured as an anode. Thus, the MEL being configured using the communication sequence 601 includes four groups of electrodes, with each group including four electrodes.

For the bits within the groups of bits $608_a$-$608_d$ of the first communication sequence of bits 601, there are two possible bit-types, with one of the bit-types specifying that an electrode is to be configured as an anode, and the other one of the bit-types specifying that the electrode is not to be configured as an anode. The two possible bit types in the first communication sequence of bits 601 include a 0 bit type and a 1 bit type. For example, a 1 bit type can specify that an electrode is to be configured as an anode, and a 0 bit type can specify that an electrode is not to be configured as an anode. The opposite can alternatively be used.

As an example of ordering within the first communication sequence of bits 601, but not limited thereto, the 4-bit op code 606 follows the start overhead 604, the groups of bits $608_a$-$608_d$ follow the 4-bit op code 606, and the end overhead 614 follows the groups of bits $608_a$-$608_d$.

Figure 6B:
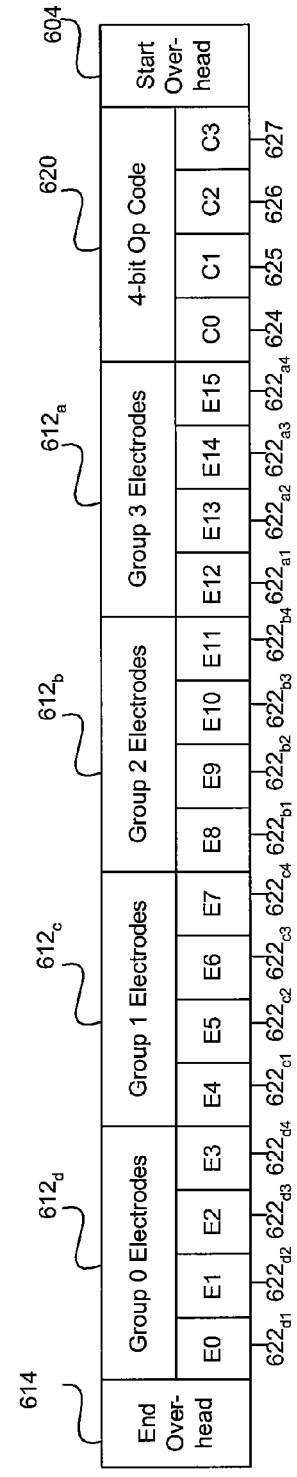

FIG. 6B schematically illustrates the second communication sequence of bits 602 that can be sent at step 502. The second communication sequence of bits 602 comprises the start overhead 604 that identifies a start of the second communication sequence of bits 602 and the end overhead 614 that identifies an end of the second communication sequence of bits 602.

Following the start overhead 604 is a 4-bit op code 620 that includes bit positions 624-627. The 4-bit op code 620 can instruct the control and switching circuitry 420 to perform one of a plurality of commands. For example, the MEL being configured using the communication sequence of bits 602 includes the 4-bit op code 620 that can instruct the control and switching circuitry 420 such that the communication sequence of bits 602 can be used to configure zero, one or more electrodes of a group of electrodes as a cathode. The op code 620 can alternatively include more or less than 4-bits.

A first group of bits $612_a$ includes bit positions $622_{a1}$-$622_{a4}$. A second group of bits $612_b$ includes bit positions $622_{b1}$-$622_{b4}$. Also shown are a third group of bits $622_c$ and a fourth group of bits $622_d$, including bit positions $622_{c1}$-$622_{c4}$ and $622_{d1}$-$622_{d4}$, respectively. Each bit, within each group of bits $612_a$-$612_d$ of the second communication sequence of bits 602 that corresponds to one of the N groups of electrodes, has a bit-location that corresponds to one of the electrodes within the group of electrodes, and has a bit-type that specifies whether or not the electrode corresponding to the bit-location is to be configured as a cathode. Thus, the MEL being configured using the communication sequence 602 includes four groups of electrodes, with each group including four electrodes.

For the bits within groups of bits $612_a$-$612_d$ of the second communication sequence of bits 602, there are two possible bit-types, with one of the bit-types specifying that an electrode is to be configured as a cathode, and the other one of the bit-types specifying that the electrode is not to be configured as a cathode. The two possible bit types in the second communication sequence of bits 602 include a 0 bit type and a 1 bit type. For example, a 1 bit type can specify that an electrode is to be configured as an anode, and a 0 bit type can specify that an electrode is not to be configured as an anode. The opposite can alternatively be used.

As an example of ordering within the second communication sequence of bits 602, but not limited thereto, the 4-bit op code 620 follows the start overhead 604, the groups of bits $612_a$-$612_d$ follow the 4-bit op code 620, and end overhead 614 follows the groups of bits $612_a$-$612_d$.

The first communication sequence of bits 601 can be sent before or after the second communication sequence of bits 602 depending on implementation. In an embodiment, the sending of the first and second communication sequences are performed without any time delay therebetween, as mentioned above. In another embodiment, there can be a delay between the sending of the first and second communication sequences, as also described above.

As discussed in FIG. 4A, an MEL can include control and switching circuitry 420 associated with each of the N groups of electrodes. Each control and switching circuitry $420_a$-$420_d$ is connected to conductors (e.g., 414 and 416), over which communication sequences can be sent to the control and switching circuitry associated with each of the N groups of electrodes. As an example, the first and second communication sequences of bits can be sent via conductors 414 and 416 of the MEL 404 to the respective control and switching circuitry $420_a$-$420_d$ associated with each of the N groups of electrodes.

For each of the N groups of electrodes, the control and switching circuitry 420 associated with the group of electrodes can be used to detect one of the N groups of bits within the first communication sequence of bits 601 that corresponds to the group of electrodes. Once the appropriate one of the N groups of bits (within the first communication sequence of bits 601 that corresponds to the group of electrodes) is detected, the control and switching circuitry 420 configures zero, one or more of the M electrodes of the group of electrodes as an anode, as defined by the bits. The detecting of the correct one of the N groups of bits (within the first communication sequence of bits 601 that correspond to the group of electrodes) can be based on a number of wait-states waited following the one or more bits (e.g., the op code 606) within the first communication sequence of bits 601 that identify that the first communication sequence of bits 601 is being used to configure electrodes as an anode.

For example, referring to FIGS. 4A-4C and 6A, once the control and switching circuitry $420_a$ detects the 4 bit op code 606, the control and switching circuitry $420_a$ can be configured to wait zero wait-states (i.e., not wait) after the op code 606 before detecting the group of bits $608_a$ of the first communication sequence 601 that are to be used to configure zero, one or more of the group of electrodes $412_a$ as an anode. The control and switching circuitry $420_b$ can be configured to wait one wait-state after the op code 606 before detecting the group of bits $608_b$ of the first communication sequence 601 that are to be used to configure zero, one or more of the group of electrodes $412_b$ as an anode. The control and switching circuitry $420_c$ can be configured to wait two wait-states after the op code 606 before detecting the group of bits 608c of the first communication sequence 601 that are to be used to configure zero, one or more of the group of electrodes $412_c$ as an anode. The control and switching circuitry $420_d$ can be configured to wait three wait-states after the op code 606 before detecting the group of bits $608_d$ of the first communication sequence 601 that are to be used to configure zero, one or more of the group of electrodes $412_d$ as an anode. In the embodiment just described, the control and switching circuitry $420_a$ most distal the pacemaker/ICD is configured to wait the least amount of wait states, and the control and switching circuitry $420_d$ most proximal the pacemaker/ICD is configured to wait the most amount of wait states. Alternatively, the reverse can be true. For example, the control and switching circuitry $420_d$ most proximal the pacemaker/ICD can be configured to wait zero wait states before detecting the group of bits of the first communication sequence 601 that are to be used to configure zero, one or more of the group of electrodes $412_d$ as an anode, and the control and switching circuitry $420_a$ most distal the pacemaker/ICD can be configured to wait three wait states before detecting the group of bits of the first communication sequence 601 that are to be used to configure zero, one or more of the group of electrodes $412_a$ as an anode. Other variations are also possible, and within the scope of the present invention.

The control and switching circuitry 420 associated with the group of electrodes can also be used to detect one of the N groups of bits within the second communication sequence of bits 602 that corresponds to the group of electrodes. Once the appropriate one of the N groups of bits (within the second communication sequence of bits 602 that corresponds to the group of electrodes) is detected, the control and switching circuitry 420 configures zero, one or more of the M electrodes of the group of electrodes as a cathode as defined by the bits. The detecting of the one of the N groups of bits within the second communication sequence of bits 602 that correspond to the group of electrodes can be based on a number of wait-states waited following the one or more bits (e.g., the op code 620) within the second communication sequence of bits 602 that identify that the second communication sequence of bits 602 is being used to configure electrodes as a cathode. Examples of this are explained above when discussing wait-states and the first communication sequence 601.

Specific embodiments of the present invention are useful for configuring a MEL. While MELs are especially useful for pacing (and/or shocking) and sensing in the left ventricle of a patient's heart, such leads can be used for pacing (and/or shocking) and sensing in other cardiac chambers.

Embodiments of the present invention can be used for the initial set-up of a MEL, i.e., at the time of implantation of the MEL. Additionally, or alternatively, embodiments of the present invention can be used to reconfigure a MEL during a patient's follow up visit to a medical facility. Such reconfigurations can be useful where lead placement may have moved, where fibrotic encapsulation of electrodes can occur after implantation, etc. It is also possible that such reconfiguration can be performed autonomously by the implanted device, without any assistance of an external device.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIG. 5 without substantially changing the overall events and results.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A method for configuring a multi-electrode lead (MEL) that includes N groups of electrodes, with each of the N groups of electrodes including at least M electrodes, where $N \geq 2$ and $M \geq 2$, the method comprising:

sending, via the MEL, a first communication sequence of bits that includes N groups of bits, with each of the N groups of bits corresponding to a different one of the N groups of electrodes and specifying which electrode(s), if any, within the group of electrodes is to be configured as an anode; and sending, via the MEL, a second communication sequence of bits that includes N further groups of bits, with each of the N further groups of bits corresponding to a different one of the N groups of electrodes and specifying which electrode(s), if any, within the group of electrodes is to be configured as a cathode.

2. The method of claim 1, wherein:

the sending of the first communication sequence of bits occurs before the sending of the second communication sequence of bits; or the sending of the second communication sequence of bits occurs before the sending of the first communication sequence of bits.

3. The method of claim 2, wherein:

the sending of the first and second communication sequences are performed without any time delay therebetween; or the sending of the first and second communication sequences are performed with a time delay therebetween.

4. The method of claim 1, wherein:

the first communication sequence includes, in addition to the N groups of bits, one or more bits that identify that the first communication sequence is being used to configure electrodes as an anode; and the second communication sequence includes, in addition to the N further groups of bits, one or more bits that identify that the second communication sequence is being used to configure electrodes as a cathode.

5. The method of claim 4, wherein:

the first communication sequence also includes header bits that identify a start of the first communication sequence and trailer bits that identify an end of the first communication sequence; and the second communication sequence also includes header bits that identify a start of the second communication sequence and trailer bits that identify an end of the second communication sequence;

wherein within the first communication sequence, the one or more bits that identify that the first communication sequence is being used to configure electrodes as an anode follow the header bits, the N groups of bits follow the one or more bits that identify that the first communication sequence is being used to configure electrodes as an anode, and the trailer bits follow the N groups of bits; and wherein within the second communication sequence, the one or more bits that identify that the second communication sequence is being used to configure electrodes as a cathode follow the header bits, the N further groups of bits follow the one or more bits that identify that the second communication sequence is being used to configure electrodes as a cathode, and the trailer bits follow the N further groups of bits.

6. The method of claim 1, wherein:

the first of the N groups of bits within each of the communication sequences is used to configure one of the N groups of electrodes most proximal a device used to perform the sending of the communication sequences; and the last of the N groups of bits within each of the communication sequences is used to configure one of the N groups of electrodes most distal the device used to perform the sending of the communication sequences.

7. The method of claim 1, wherein:

the first of the N groups of bits within each of the communication sequences is used to configure one of the N groups of electrodes most distal the device used to perform the sending of the communication sequences; and the last of the N groups of bits within each of the communication sequences is used to configure one of the N groups of electrodes most proximal the device used to perform the sending of the communication sequences.

8. The method of claim 1, wherein:

each bit, within each group of bits of the first communication sequence that corresponds to one of the N groups of electrodes, has a bit-location that corresponds to one of the electrodes within the group of electrodes, and has a bit-type that specifies whether or not the electrode corresponding to the bit-location is to be configured as an anode; and each bit, within each further group of bits of the second communication sequence that corresponds to one of the N groups of electrodes, has a bit-location that corresponds to one of the electrodes within the group of electrodes, and has a bit-type that specifies whether or not the electrode corresponding to the bit-location is to be configured as a cathode.

9. The method of claim 8, wherein:

for the bits within the N groups of bits of the first communication sequence there are two possible bit-types, with one of the bit-types specifying that an electrode is to be configured as an anode, and the other one of the bit-types specifying that the electrode is not to be configured as an anode; and for the bits within the N further groups of bits of the second communication sequence there are two possible bit-types, with one of the bit-types specifying that an electrode is to be configured as a cathode, and the other one of the bit-types specifying that the electrode is not to be configures as a cathode.

10. The method of claim 9, wherein the two possible bit types in the first and second communication sequences include a 0 bit type and a 1 bit type.

11. The method of claim 1, wherein the MEL also includes separate control circuitry associated with each of the N groups of electrodes, and a bus over which communication sequences can be sent to the control circuitry associated with each of the N groups of electrodes, and wherein:
the steps of sending the first and second communication sequences comprise sending the first and second communication sequences via the bus of the MEL to the control circuitry associated with each of the N groups of electrodes.

12. The method of claim 11, further comprising, for each of the N groups of electrodes, using the control circuitry associated with the group of electrodes to perform the following:
detecting one of the N groups of bits within the first communication sequence that corresponds to the group of electrodes;
configuring zero, one or more of the M electrodes of the group of electrodes as an anode, in accordance with an anode configuration defined by the one of the N groups of bits corresponding to the group of electrodes;
detecting one of the N further groups of bits within the second communication sequence that correspond to the group of electrodes; and
configuring zero, one or more of the M electrodes of the group of electrodes as a cathode, in accordance with a cathode configuration defined by the one of the N further groups of bits corresponding to the group of electrodes.

13. The method of claim 12, wherein for each of the N groups of electrodes:
the detecting of the one of the N groups of bits within the first communication sequence that correspond to the group of electrodes is based on a number of wait-states waited following the one or more bits within the first communication sequence that identify that the first communication sequence is being used to configure electrodes as an anode; and
the detecting of the one of the N groups of bits within the second communication sequence that correspond to the group of electrodes is based on a number of wait-states waited following the one or more bits within the second communication sequence that identify that the second communication sequence is being used to configure electrodes as a cathode.

14. The method of claim 13, wherein:
each weight state corresponds to how long it takes the control circuitry associated with the group of electrodes to clock in M bits; and
the number of wait-states waited is an integer between and inclusive of 0 and N−1.

15. An implantable device for use with a multi-electrode lead (MEL),
wherein the MEL includes
N groups of electrodes, with each of the N groups including at least M electrodes, where N≧2 and M≧2,
control circuitry associated with each of the N groups of electrodes, and
a bus over which communication sequences can be sent to the control circuitry associated with each of the N groups of electrodes,
the implantable device comprising:
a controller adapted to
send to the control circuitry associated with each of the N groups of electrodes, via the bus of the MEL, a first communication sequence of bits that includes N groups of bits, with each of the N groups of bits corresponding to a different one of the N groups of electrodes and specifying which electrode(s), if any, within the group of electrodes is to be configured as an anode, and
send to the control circuitry associated with each of the N groups of electrodes, via the MEL, a second communication sequence of bits that includes N further groups of bits, with each of the N further groups of bits corresponding to a different one of the N groups of electrodes and specifying which electrode(s), if any, within the group of electrodes is to be configured as a cathode; and
a pulse generator adapted to generate stimulation pulses that are to be delivered to via the MEL configured in accordance with the first and second communication sequences.

16. The implantable device of claim 15, wherein the controller can send the first communication sequence of bits before or after the second communication sequence of bits.

17. The implantable device of claim 15, wherein the controller can send the first and second communication sequences with or without any time delay therebetween.

18. The implantable device of claim 15, wherein the controller is adapted to:
send as part of the first communication sequence, in addition to the N groups of bits, one or more bits that identify that the first communication sequence is being used to configure electrodes as an anode; and
send as part of the second communication sequence, in addition to the N further groups of bits, one or more bits that identify that the second communication sequence is being used to configure electrodes as a cathode.

19. The implantable device of claim 18, wherein the controller is adapted to:
send as part of the first communication sequence, header bits that identify a start of the first communication sequence and trailer bits that identify an end of the first communication sequence; and
send as part of the second communication sequence, header bits that identify a start of the second communication sequence and trailer bits that identify an end of the second communication sequence.

20. A method for configuring a multi-electrode lead (MEL) that includes N groups of electrodes, with each of the N groups of electrodes including at least M electrodes, where N≧2 and M≧2, the method comprising:
sending, via the MEL, a communication sequence of bits that includes
one or more bits that identify that the communication sequence is being used to configure electrodes as one of an anode and a cathode; and
N groups of bits, with each of the N groups of bits corresponding to a different one of the N groups of electrodes and specifying which electrode(s), if any, within the group of electrodes is to be configured as the one of the anode and cathode.

* * * * *